United States Patent [19]

Thill et al.

[11] 4,016,171

[45] Apr. 5, 1977

[54] PROCESS FOR MAKING 2-VINYL-2-OXAZOLINES

[75] Inventors: Bruce P. Thill; Janet N. Paige, both of Midland, Mich.

[73] Assignee: The Dow Chemical Company, Midland, Mich.

[22] Filed: Sept. 14, 1972

[21] Appl. No.: 288,914

[52] U.S. Cl. .......................................... 260/307 F
[51] Int. Cl.² ..................................... C07D 263/12
[58] Field of Search .............................. 260/307 F

[56] References Cited

UNITED STATES PATENTS 3,331,851   7/1967   Bassiri ................................. 260/307
3,483,145   12/1969   Levy et al. ............................ 260/2

OTHER PUBLICATIONS

Fieser et al.—"Advanced Organic Chemistry"—Reinhold Publ. Corp., New York, pp. 215–216 (1961).
March —"Advanced Organic Chemistry: Reactions, Mechanisms, and Structures"—McGraw Hill — p. 745 (1968).

*Primary Examiner*—Raymond V. Rush
*Attorney, Agent, or Firm*—L. Wayne White

[57] ABSTRACT

2-Vinyl-2-oxazolines are prepared in the novel process comprising reacting (1) an N-(2-haloalkyl)-3-halopropionamide with (2) at least 2 equivalents of an inorganic base per mole of (1). The process is conducted under substantially anhydrous conditions and in the presence of an alkylene glycol or a polyalkylene glycol.

13 Claims, No Drawings

PROCESS FOR MAKING 2-VINYL-2-OXAZOLINES

BACKGROUND OF THE INVENTION

The 2-vinyl-2-oxazolines form a known class of compounds which are useful as epoxy curing agents, as reactive functional monomers, as plasticizers, etc. Additionally, they can be homopolymerized or interpolymerized with other vinyl monomers (e.g. ethyl acrylate, acrylamide, styrene, etc.) to form many useful polymers.

The 2-vinyl-2-oxazolines and other 2-substituted 2-oxazolines along with methods of preparation have been described, for example, in U.S. Pat. Nos. 2,831,858, 3,331,851 and 3,505,297. However, not all methods of preparing 2-substituted 2-oxazolines have been adaptable to the preparation of 2-vinyl-2-oxazolines.

A need therefore exists for a process for preparing 2-vinyl-2-oxazolines in high yield and purity and preferably in a 1-step process.

SUMMARY OF THE INVENTION

A novel process for making 2-vinyl-2-oxazolines has now been discovered. The process comprises reacting by contacting (1) an N-(2-haloalkyl)-3-halopropionamide with (2) at least two equivalents of an inorganic base. The process is conducted under substantially anhydrous conditions and in the presence of a mono- or polyhydric aliphatic solvent. Typically, the process is conducted under conditions of temperature and pressure such that the desired product is distilled from the reaction mixture as it is formed.

THE HALOPROPIONAMIDES

The reactants in the subject process are 2-haloalkyl-3-halopropionamides. By "halo" is meant chloro or bromo. Such reactants may suitably vary in carbon content but generally have an aggregative content of from 5 to about 20 carbon atoms. Preferred reactants have a total carbon content of from 5 to about 10 carbon atoms; most preferably, only 5 carbon atoms. Each member of the known class of 2-haloalkyl-3-halopropionamides is suitable for use herein. Examples of suitable reactants include A—$CH_2CH_2$—Cl, A—CH($CH_3$)—$CH_2Cl$, A—CH($C_4H_9$)—$CH_2Cl$, A—CH($C_6H_{13}$)—$CH_2Cl$, A—CH($C_{12}H_{25}$)—$CH_2Cl$, A—$CH_2$—CHCl—$CH_3$, A—$CH_2$CHCl—$C_3H_7$, A—$CH_2$—CH—Cl—$C_8H_{17}$, A—$CH_2$—CHCl—$C_{12}H_{25}$, A—CH($CH_3$)—CHCl—$CH_3$, A—CH($C_2H_5$)—CHCl—$C_2H_5$, A—CH($CH_3$)—CHCl—$C_4H_9$, and the like wherein "A—" represents Cl—$CH_2CH_2$—C(O)—NH— and the corresponding bromo compounds. Mixed halo compounds, such as Cl—$CH_2CH_2$—NH—C(O)—$CH_2CH_2$—Br, are likewise suitable.

While the preparation of these reactants does not constitute a part of the subject invention, it is noted that they can be prepared by reacting a delta lactone with thionyl halide to produce a 3-halopropionyl halide which is subsequently reacted with an aziridine to form the corresponding N-(2-haloethyl)-3-halopropionamide. Other known methods can likewise be employed.

THE INORGANIC BASES

The subject process involves, at least in part, dehydrohalogenation. A wide variety of inorganic bases have been previously used to promote dehydrohalogenation, any one of which is suitable for use herein. The most common bases, however, are the alkali and alkaline earth metal oxides, hydroxides and carbonates. These particular bases are thus preferred in the instant process and the sodium and potassium carbonates are most preferred.

Examples of suitable bases include lithium, sodium and potassium oxides, hydroxides and carbonates; and magnesium, calcium, strontium and barium oxides, hydroxides and carbonates; and other like compounds.

RATIO OF REACTANTS

The stoichiometry of the reaction requires two equivalents of base per mole of halopropionamide reactant. More or less than the stoichiometric amount of base can obviously be used but the product yield is maximized by using at least a stoichiometric amount of base. Thus, a stoichiometric amount or excess of base is preferred, (e.g. from 2 to about 5 equivalents per mole of halo-propionamide).

When a carbonate is used, we prefer at least two moles of carbonate per mole of halopropionamide. This minimizes the formation of water and/or $H_2CO_3$ which could lead to undesirable by-products at elevated temperatures.

THE REACTION MEDIUM

The reaction medium is an alkylene glycol (2–4 carbon atoms) or a polymer thereof. If a polyalkylene glycol is used, it must be liquid at reaction temperature. The reactants are normally soluble or dispersible in such compounds. Examples of compounds which may be used as the reaction medium include ethylene glycol, propylene glycol, butylene glycol and homo-and interpolymers thereof which are normally prepared, for instance, by reacting said glycol (or water) with the appropriate alkylene oxide(s) in the presence of a base (e.g. KOH). Random and block interpolymer may be used. The alkylene glycols and oligomers thereof (e.g. from 2 to about 10 repeating alkylene oxide units) are preferred. Ethylene glycol, propylene glycol, diethylene glycol and dipropylene glycol are most preferred.

OTHER PARAMETERS

The reaction is conducted under substantially anhydrous conditions and generally at a temperature of from about 70° to about 140° C. A preferred reaction rate is achieved at temperatures of from about 85° to about 120° C. Atmospheric and subatmospheric pressures are normally used. The combination of temperature and pressure is preferably chosen such that the desired product is distilled from the reaction mixture essentially as it is formed. In which case, the product distillate is neat or aqueous depending upon the base used. It is obtained neat when excess carbonate is used and aqueous when other bases (e.g. KOH) are used. Any water formed in the course of the reaction normally co-distills with the desired product and can be removed therefrom by conventional techniques (e.g. by azeotropic distillation with $CH_2Cl_2$ or $C_6H_6$).

EXPERIMENTAL

The following examples further illustrate the invention.

EXAMPLE 1

To a reaction vessel equipped for vacuum distillation was charged N-(2-chloroethyl)-3-chloro-propionamide (126.4 g; 0.75 mole), anhydrous sodium carbonate (157 g; 1.5 mole), ethylene glycol 750 ml. and 0.05 g. of phenothiazine. The pressure in the reaction vessel was reduced to 45–50 mm. Hg absolute and the temperature slowly raised to 119° C, with stirring. The distillate, amounting to 59.9 g. (82%) was identified as 2-vinyl-2-oxazoline by comparison of its infrared and nuclear magnetic resonance spectra and vapor phase chromatography retention time with an authentic sample. The product was stabilized against polymerization by the addition of 0.1% phenothiazine inhibitor.

EXAMPLE 2

Proceeding in the equipment and fashion analogous to Example 1, 2-vinyl-2-oxazoline was obtained in 58.8% yield by reacting N-(2-chloroethyl)-3-chloropropionamide (17.0 g.) with anhydrous sodium carbonate (21.2 g.) in the presence of 0.01 g. phenothiazine and 100 ml. diethylene glycol.

EXAMPLE 3

In like manner, 2-vinyl-2-oxazoline was obtained in 42% yield by reacting N-(2-chloroethyl)-3-chloropropionamide (14.7 g., .0986 mole) with anhydrous sodium carbonate (18.3 g., 0.172 mole) in the presence of 0.01 g. phenothiazine and 87 ml. dipropylene glycol.

EXAMPLE 4

An isomeric mixture of 2-vinyl-4-(or 5)-methyl-2-oxazoline was obtained in 54% yield by reacting a mixture of N-(1(or 2)-methyl-2-chloroethyl)-3-chloropropionamide with sodium carbonate in ethylene glycol, analogous to Example 1.

Other products described herein are similarly prepared in accordance with the above description of the invention.

I claim:
1. A process for making a 2-vinyl-2-oxazoline comprising the steps of
   A. reacting by contacting in liquid phase
      1. an N-(2-haloalkyl)-3-halopropionamide having a total carbon content of from 5 to about 20 carbon atoms, with
      2. at least about 2 moles of an alkali or alkaline earth metal carbonate or an alkali metal hydroxide per mole of (1) or at least about 1 mole of alkaline earth metal hydroxide per mole of (1);
      step (A) being conducted under substantially anhydrous conditions and in the presence of an alkylene glycol of 2–4 carbon atoms or apolymer thereof; and
   B. recovering the 2-vinyl-2-oxazoline product.
2. The process defined by claim 1 wherein said glycol is ethylene glycol, propylene glycol or oligomers thereof having from 2 to about 10 repeating alkylene oxide units.
3. The process defined by claim 2 wherein said glycol is ethylene glycol, propylene glycol, diethylene glycol or dipropylene glycol.
4. The process defined by claim 1 wherein (2) is sodium or potassium carbonate.
5. The process defined by claim 4 wherein (2) is sodium carbonate.
6. The process defined by claim 1 wherein (1) has a total carbon content of from 5 to 10 carbon atoms.
7. The process defined by claim 6 wherein (1) is N-(2-haloethyl)-3-halopropionamide.
8. The process defined by claim 1 wherein the reaction temperature for step (A) is from about 70° to about 140° C.
9. The process defined by claim 8 wherein said temperature is from about 85° to about 120° C.
10. The process defined by claim 1 wherein step (B) is conducted by distilling the product from the reaction mixture essentially as it is formed.
11. The process defined by claim 10 wherein (1) is N-(2-chloroethyl)-3-chloropropionamide, (2) is sodium carbonate, and wherein step (A) is conducted at a temperature of from about 85° to about 120° C in the presence of ethylene glycol, propylene glycol, diethylene glycol or dipropylene glycol.
12. The process defined by claim 11 wherein step (A) is conducted in the presence of ethylene glycol.
13. The process defined by claim 12 wherein said process is conducted in the presence of a small but sufficient amount of phenothiazine to inhibit polymerization of the product.

* * * * *